United States Patent [19]
Douglas

[11] Patent Number: 6,090,128
[45] Date of Patent: Jul. 18, 2000

[54] BIFURCATED VASCULAR GRAFT DEPLOYMENT DEVICE

[75] Inventor: Myles S. Douglas, Phoenix, Ariz.

[73] Assignee: Endologix, Inc., Irvine, Calif.

[21] Appl. No.: 08/802,478

[22] Filed: Feb. 20, 1997

[51] Int. Cl.⁷ .............................. A61B 17/00; A61F 2/06
[52] U.S. Cl. ................................................ 606/198; 623/1
[58] Field of Search .................................... 606/195, 198, 606/191, 194, 200; 623/1, 12, 11

[56] References Cited

U.S. PATENT DOCUMENTS

| | | |
|---|---|---|
| 2,127,903 | 8/1938 | Bowen . |
| 2,845,959 | 8/1958 | Sidebotham . |
| 2,990,605 | 7/1961 | Demsyk . |
| 3,029,819 | 4/1962 | Starks . |
| 3,096,560 | 7/1963 | Liebig . |
| 3,805,301 | 4/1974 | Liebig . |
| 4,497,074 | 2/1985 | Rey et al. . |
| 4,501,263 | 2/1985 | Harbuck . |
| 4,503,568 | 3/1985 | Madras . |
| 4,592,754 | 6/1986 | Gupte et al. . |
| 4,617,932 | 10/1986 | Kornberg . |
| 4,816,028 | 3/1989 | Kapadia et al. . |
| 4,840,940 | 6/1989 | Sottiurai . |
| 4,856,516 | 8/1989 | Hillstead . |
| 4,878,906 | 11/1989 | Lindemann et al. . |
| 4,907,336 | 3/1990 | Gianturco . |
| 4,922,905 | 5/1990 | Strecker . |
| 5,019,909 | 5/1991 | Pinchuk . |
| 5,078,726 | 1/1992 | Kreamer . |
| 5,104,399 | 4/1992 | Lazarus . |
| 5,108,424 | 4/1992 | Hoffman, Jr. et al. . |
| 5,156,619 | 10/1992 | Ehrenfeld . |
| 5,178,634 | 1/1993 | Martinez . |
| 5,197,976 | 3/1993 | Herweck et al. . |
| 5,256,141 | 10/1993 | Gencheff et al. . |
| 5,275,622 | 1/1994 | Lazarus et al. . |
| 5,282,824 | 2/1994 | Gianturco . |
| 5,304,200 | 4/1994 | Spaulding . |
| 5,314,472 | 5/1994 | Fontaine . |
| 5,316,023 | 5/1994 | Palmaz et al. . |
| 5,342,387 | 8/1994 | Summers . |
| 5,360,443 | 11/1994 | Barone et al. . |
| 5,366,504 | 11/1994 | Andersen et al. . |
| 5,370,683 | 12/1994 | Fontaine . |
| 5,387,235 | 2/1995 | Chuter . |
| 5,423,886 | 6/1995 | Arru et al. . |
| 5,425,765 | 6/1995 | Tiefenbrun et al. . |
| 5,443,498 | 8/1995 | Fontaine . |
| 5,443,500 | 8/1995 | Sigwart . |

(List continued on next page.)

FOREIGN PATENT DOCUMENTS

| | | |
|---|---|---|
| 0 177 330 B1 | 6/1991 | European Pat. Off. . |
| 0 596 145 A1 | 5/1994 | European Pat. Off. . |
| 0 621 015 A1 | 10/1994 | European Pat. Off. . |
| 0 659 389 A1 | 6/1995 | European Pat. Off. . |
| 0 740 928 A2 | 11/1996 | European Pat. Off. . |
| 0 747 020 A2 | 12/1996 | European Pat. Off. . |
| 0 775 470 A1 | 5/1997 | European Pat. Off. . |
| WO 93/13825 | 7/1993 | WIPO . |
| WO 96/41589 | 12/1996 | WIPO . |
| WO 97/10777 | 3/1997 | WIPO . |

Primary Examiner—Michael Buiz
Assistant Examiner—Vikki Trinh
Attorney, Agent, or Firm—Knobbe, Martens, Olson & Bear, LLP

[57] ABSTRACT

A structurally supported bifurcated vascular graft is described having a hollow cylindrical body graft with a top end and bottom end and two hollow cylindrical limb grafts which are attached to the hollow cylindrical body graft near the top end of the body graft. One or more structural supports or stents are attached to either the interior or exterior of the body graft and limb grafts. Further, an apparatus and method for delivering a one-piece bifurcated vascular graft is also described which includes first and second hollow limb tubes for containing the limbs of a bifurcated graft, a third hollow body tube for containing the body of a graft, and a hollow delivery tube capable of encompassing the limb tubes and graft body tube.

26 Claims, 6 Drawing Sheets

U.S. PATENT DOCUMENTS

| | | | |
|---|---|---|---|
| 5,456,713 | 10/1995 | Chuter | 606/195 |
| 5,489,295 | 2/1996 | Piplani et al. . | |
| 5,496,365 | 3/1996 | Sgro . | |
| 5,507,767 | 4/1996 | Maeda et al. . | |
| 5,507,771 | 4/1996 | Gianturco . | |
| 5,522,880 | 6/1996 | Barone et al. . | |
| 5,522,881 | 6/1996 | Lentz . | |
| 5,522,883 | 6/1996 | Slater et al. . | |
| 5,545,211 | 8/1996 | An et al. . | |
| 5,562,728 | 10/1996 | Lazarus et al. . | |
| 5,578,072 | 11/1996 | Barone et al. . | |
| 5,591,229 | 1/1997 | Parodi . | |
| 5,609,625 | 3/1997 | Piplani et al. . | |
| 5,609,627 | 3/1997 | Goicoechea et al. . | |
| 5,628,788 | 5/1997 | Pinchuk . | |
| 5,632,772 | 5/1997 | Alcime et al. . | |
| 5,643,339 | 7/1997 | Kavteladze et al. . | |
| 5,647,857 | 7/1997 | Anderson et al. . | |
| 5,653,727 | 8/1997 | Wiktor . | |
| 5,653,743 | 8/1997 | Martin . | |
| 5,653,746 | 8/1997 | Schmitt . | |
| 5,653,747 | 8/1997 | Dereume . | |
| 5,662,700 | 9/1997 | Lazarus . | |
| 5,662,702 | 9/1997 | Keranen . | |
| 5,665,115 | 9/1997 | Cragg . | |
| 5,665,117 | 9/1997 | Rhodes . | |
| 5,674,241 | 10/1997 | Bley et al. . | |
| 5,674,276 | 10/1997 | Andersen et al. . | |
| 5,676,696 | 10/1997 | Marcade . | |
| 5,676,697 | 10/1997 | McDonald . | |
| 5,679,400 | 10/1997 | Tuch . | |
| 5,681,346 | 10/1997 | Orth et al. . | |
| 5,683,448 | 11/1997 | Cragg . | |
| 5,683,449 | 11/1997 | Marcade . | |
| 5,683,450 | 11/1997 | Goicoechea et al. . | |
| 5,683,451 | 11/1997 | Lenker et al. . | |
| 5,683,452 | 11/1997 | Barone et al. . | |
| 5,683,453 | 11/1997 | Palmaz . | |
| 5,690,644 | 11/1997 | Yurek et al. . | |
| 5,693,066 | 12/1997 | Rupp et al. . | |
| 5,693,084 | 12/1997 | Chuter . | |
| 5,693,086 | 12/1997 | Goicoechea et al. . | |
| 5,693,087 | 12/1997 | Parodi . | |
| 5,693,088 | 12/1997 | Lazarus . | |
| 5,695,516 | 12/1997 | Fischell et al. . | |
| 5,695,517 | 12/1997 | Marin et al. . | |
| 5,720,776 | 2/1998 | Chuter et al. | 623/1 |
| 5,723,004 | 3/1998 | Dereume et al. | 623/1 |
| 5,746,766 | 5/1998 | Edoga | 606/198 |
| 5,755,771 | 5/1998 | Penn et al. . | |
| 5,769,885 | 6/1998 | Quiachon et al. | 623/1 |

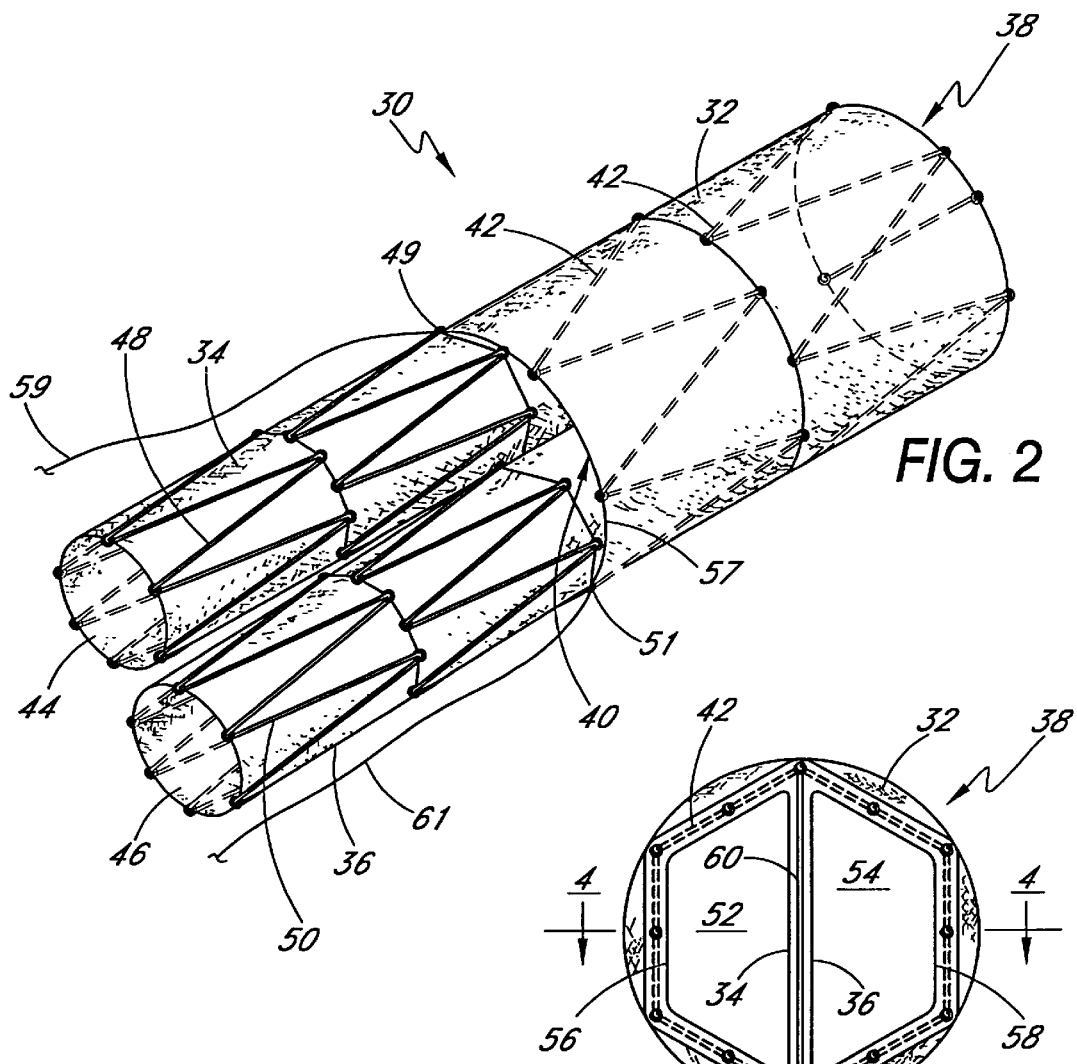
FIG. 2
FIG. 3
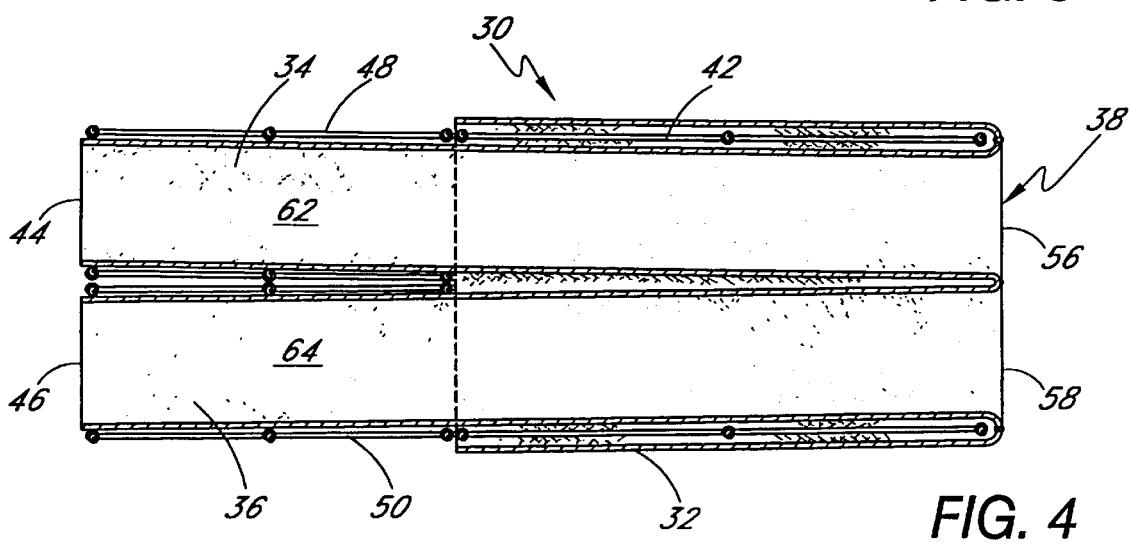
FIG. 4

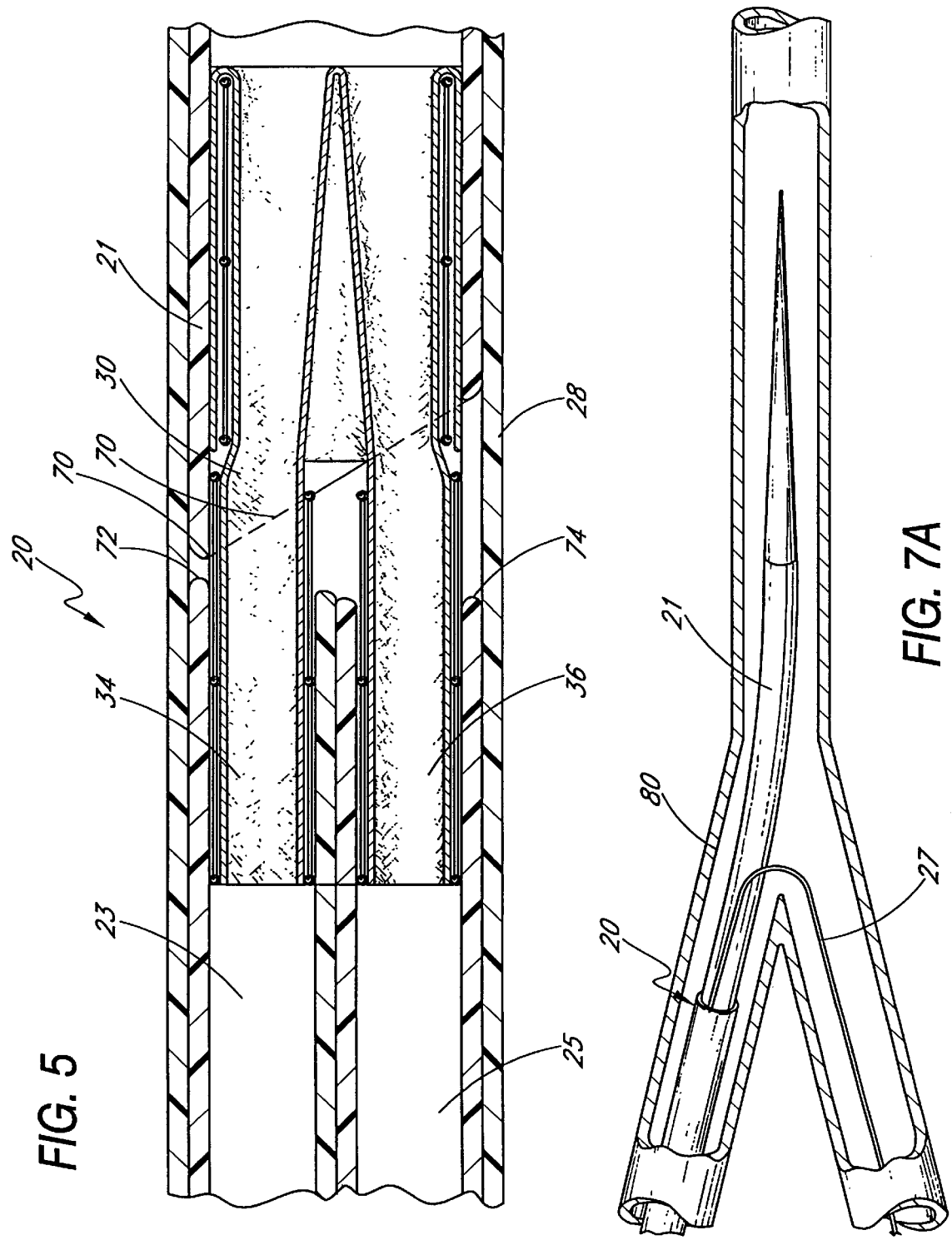

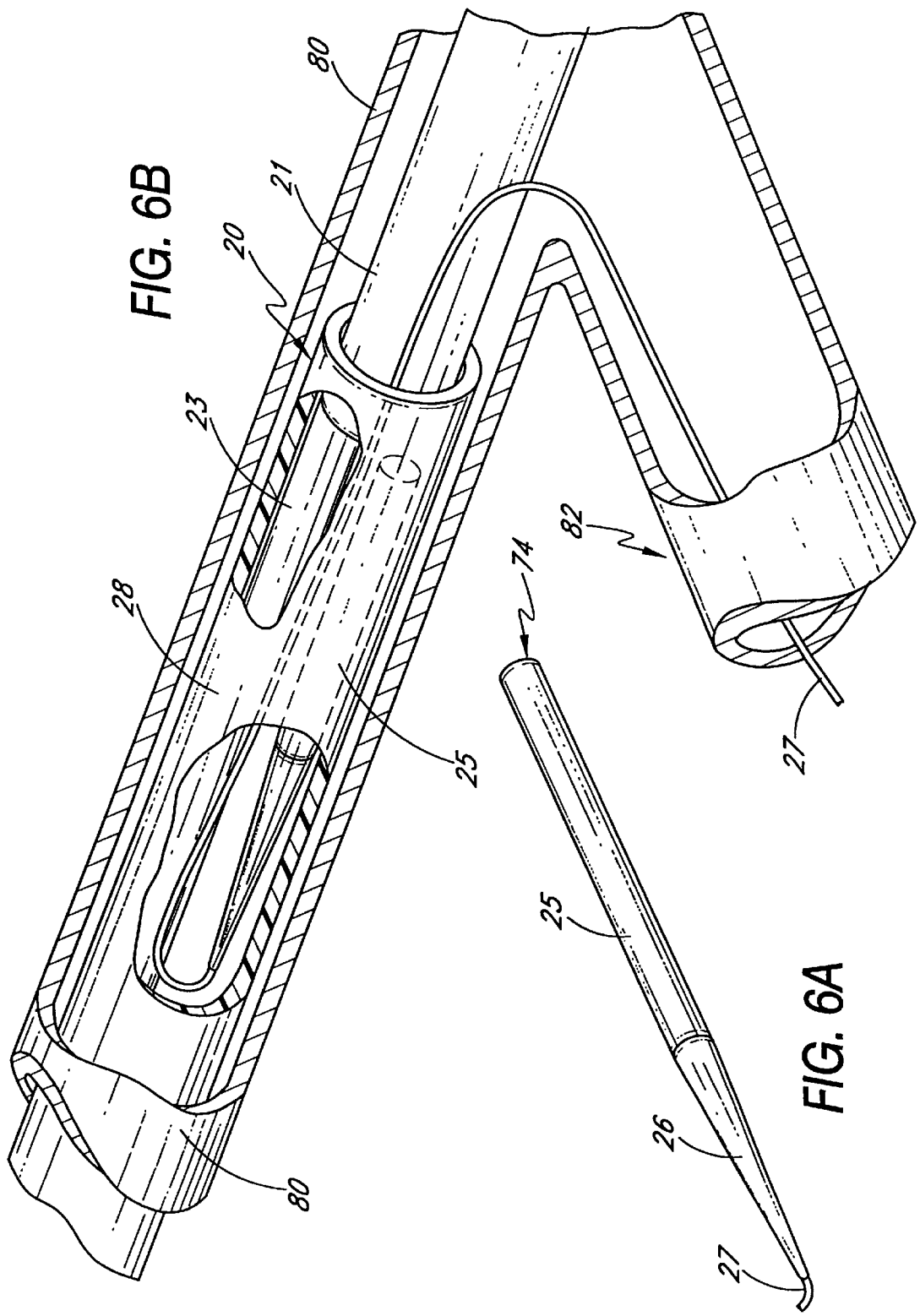

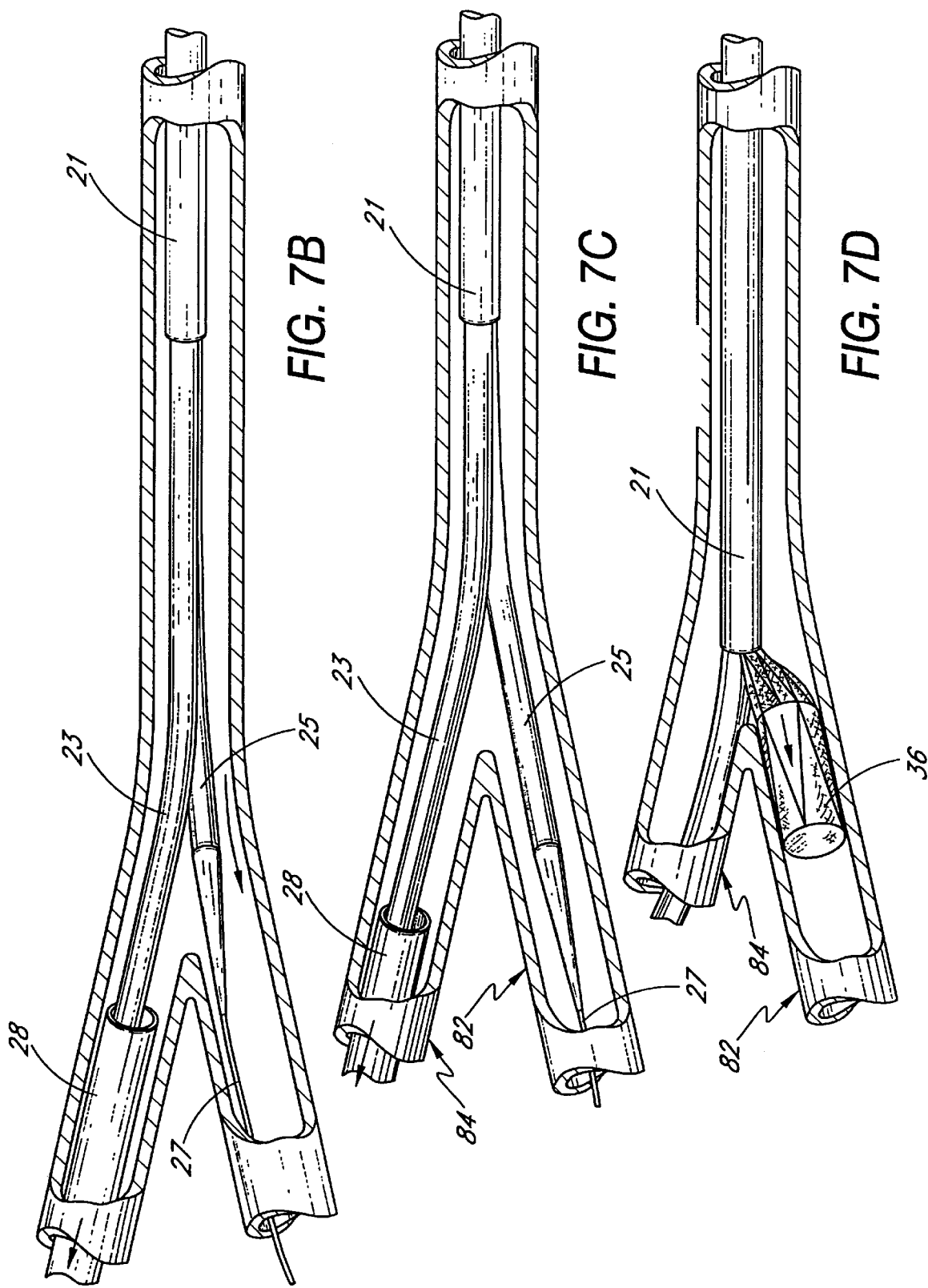

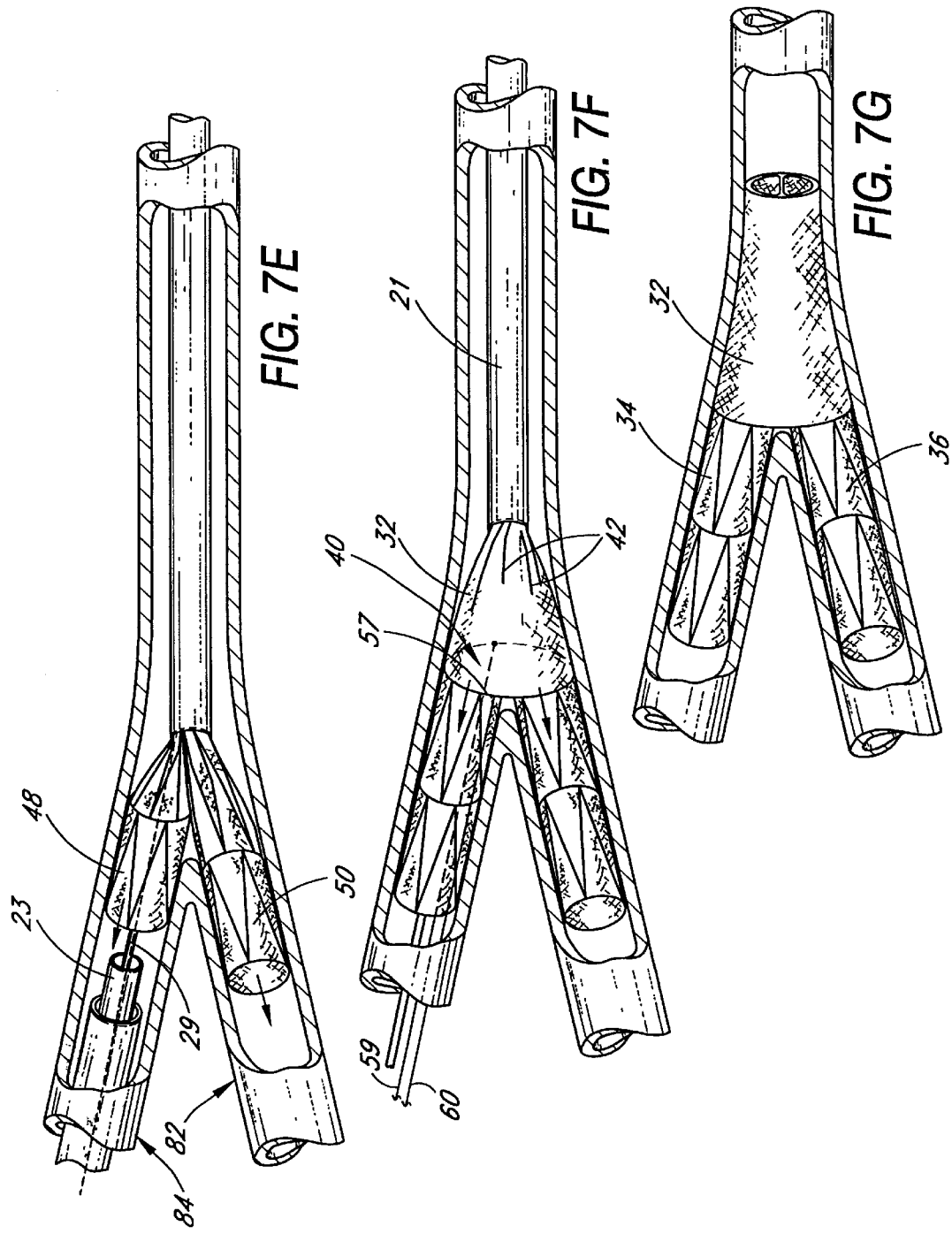

BIFURCATED VASCULAR GRAFT DEPLOYMENT DEVICE

FIELD OF THE INVENTION

The present invention generally relates to a bifurcated graft and an apparatus and method for delivering the same within the body of a patient using a minimally invasive procedure. More particularly, the present invention includes a bifurcated vascular graft having two hollow cylindrical limb grafts of an equal first diameter attached to one another along a portion of their circumferences at their first ends and a third hollow cylindrical body graft of a larger diameter circumferentially positioned over the first two hollow cylindrical limb grafts such that the remaining unconnected end circumferences of the first two hollow cylindrical limb grafts are connected about an end circumference of the third hollow cylindrical body graft thereby bisecting the diameter of the third hollow cylindrical body graft in half.

The present invention also includes an apparatus and method for delivering the bifurcated vascular graft of the present invention which includes first and second hollow limb tubes of approximately equal diameter and varying lengths for containing the two hollow cylindrical limb grafts, a third hollow body tube having a larger diameter than the first and second hollow limb tubes for containing the hollow cylindrical body graft, a metal tube for containing a guide wire, and a hollow delivery tube which is capable of encompassing the first and second hollow limb tubes, the hollow body tube, and the metal tube.

BACKGROUND OF THE INVENTION

Endoluminal repair or exclusion of aortic aneurysms has been performed for the past several years. The goal of endoluminal aortic aneurysm exclusion has been to correct this life threatening disease in a minimally invasive manner in order to effectuate a patient's quick and complete recovery. Various vascular grafts exist in the prior art which have been used to exclude aortic aneurysms. These prior art grafts have been met with varying degrees of success.

Initially, straight tube grafts were used in the abdominal aorta to exclude the aneurysmal sac from the blood stream thereby resulting in the weakened aortic wall being protected by the graft material. These straight tube grafts were at first unsupported meaning that they employed stents at their proximal and distal ends to anchor the proximal and distal ends of the graft to the healthy portions of the aorta thereby leaving a midsection of the graft or prosthesis that did not have any internal or stented support. Although this type of graft at first appeared to correct the aortic aneurysm, it met with many failures. The unsupported nature of its midsection allowed the graft to migrate distally as well as exhibit significant proximal leakage due to the enlargement of the aorta without adaptation of the graft, such as enlargement of the graft, to accommodate the change in diameter of the aorta.

Later, technical improvements in stent design led to "self-expanding" stents. In addition, latter improvements produced "Nitinol" stents which had a "memory" that was capable of expanding to a pre-determined size. Coincidentally, graft designers began to develop bifurcated grafts having limbs which extended into the iliac arteries. The development of bifurcated grafts allowed for the treatment of more complex aneurysms. With the advent of bifurcated grafts, the need for at least a one centimeter neck from the distal aspect of the aneurysmal sac to the iliac bifurcation in order to treat the aneurysm with an endoluminal graft was no longer needed. However, proximal necks of at least 0.5 to 1 centimeter distance from the renal arteries to the most proximal aspect of the aneurysm are still required.

Many bifurcated grafts are of a two piece design. These two piece designs require the insertion of a contralateral limb through a separate access site. These types of grafts are complex to deploy and have the potential for leakage at the connection site of the two limbs of the graft. One piece bifurcated grafts have also been designed. However, there deployment is still somewhat complicated and has torsion tendencies.

One piece bifurcated grafts are well known in the art. For example, U.S. Pat. No. 2,845,959 discloses a one piece seamless woven textile bifurcated tube for use as an artificial artery. Yarns of varying materials can be used to weave the bifurcated graft including nylon and plastic yarns. U.S. Pat. Nos. 3,096,560 and 3,029,819 issued to Liebig and Starks, respectively, disclose woven one piece bifurcated grafts which are constructed by performing specific types of winding and weaving about a smooth bifurcated mandrel.

U.S. Pat. No. 4,497,074 describes a one piece bifurcated graft which is made from a preformed support in the shape of the bifurcated graft (i.e. mould). In a first stage, a gel enabling a surface state close to that of the liquid-air interface to be obtained at the gel-air interface is deposited by dipping or coating the preform with a sol which is allowed to cool. A hardenable flexible material such as a silicone elastomer by dipping or spraying the material on the mould in a second stage. Finally, after hardening of the material, the prosthesis is removed from the mould. In U.S. Pat. No. 4,816,028 issued to Kapadia et al., there is shown a one piece woven bifurcated vascular graft having a plurality of warp threads running in the axial direction and a plurality of weft threads running in the transverse direction. Further, U.S. Pat. No. 5,108,424 issued to Hoffman, Jr. et al. discloses a one piece bifurcated collagen-impregnated dacron graft. The bifurcated graft includes a porous synthetic vascular graft substrate formed by knitting or weaving with at least three applications of dispersed collagen fibrils.

The Herweck et al. patent, U.S. Pat. No. 5,197,976, discloses a continuous one piece bifurcated graft having plural longitudinally parallel tube structures which are attached to one another over at least a portion of their longitudinal exteriors. The tube structures can be manually separated to form a branched tubular structure. The prosthesis is manufactures by paste forming and stretching and/or expanding highly crystalline unsintered polytetrafluoroethylene (PTFE). Paste forming includes mixing the PTFE resin with a lubricant, such as mineral spirits, and then forming the resin by extrusion into shaped articles.

Although all of the above described one piece bifurcated grafts have eliminated the problems of leakage and graft failure at the suture or juncture site associated with two piece bifurcated grafts which join together two separate grafts to form the bifurcated graft, problems still exist with these one piece bifurcated grafts. For example, the previously described one piece bifurcated grafts do not include an integral support structure to prevent the deformation, twisting or collapse of the graft limbs. Further, the same problems with graft migration that existed with straight tube grafts still exist with the one piece bifurcated grafts. Accordingly, there is a need for a stable and durable bifurcated vascular graft which is structured to prevent the migration of the graft and the deformation and obstruction of the blood flow through the limbs of the bifurcated graft.

Endoluminal implantation is a common technique for implanting vascular grafts. Typically, this procedure involves percutaneously inserting a vascular graft or prosthesis by using a delivery catheter. This process eliminates the need for major surgical intervention thereby decreasing the risks associated with vascular and arterial surgery. Various catheter delivery systems for prosthetic devices are described in the prior art.

For example, bifurcated vascular grafts have been created by combining grafts with stents on delivery systems in order to secure the graft ends to the blood vessel thereby stabilizing the bifurcated graft. In U.S. Pat. No. 5,360,443 issued to Barone et al. A method for repairing an abdominal aortic aneurysm is described. The method comprises the steps of 1) connecting an expandable and deformable tubular member, such as a stent, to each of the tubular passageways of a bifurcated graft, 2) disposing the bifurcated graft and deformable tubular members within the aortic and iliac arteries, and 3) expanding and deforming each deformable tubular member with a catheter to secure each tubular passageway of the bifurcated graft within the appropriate artery. This reference only discloses a catheter delivery method for deploying the aortic portion of the bifurcated graft. The same catheter is supposedly used to also expand and secure the associated stents within the iliac arteries. The Palmaz et al. patent, U.S. Pat. No. 5,316,023, describes a method and apparatus for repairing an abdominal aortic aneurysm in an aorta having two iliac arteries. This method includes the steps of connecting a first tubular graft to a first deformable and expandable tubular member, connecting a second tubular graft to a second deformable and expandable tubular member, disposing the first tubular graft and first tubular member upon a first catheter having an inflatable portion, disposing the second tubular graft and second tubular member upon a second catheter having an inflatable portion, intraliminal delivering the first and second tubular grafts, tubular members and catheters to the aorta and disposing at least a portion of each tubular graft within the abdominal aortic aneurysm, and expanding the tubular members with the inflatable catheters to secure them and at least a portion of their associated tubular grafts within the aorta. This patent reference employs two separate unconnected straight grafts which are employed within an aorta to form a bifurcated graft.

Further, U.S. Pat. No. 4,617,932 issued to Kornberg discloses a device for inserting a graft into an artery comprising a plurality of nested tubes each having an upper and lower end. A first outer tube has a means for guiding and positioning an arm means at its upper end. The arm means is movably attached to the upper end of another tube located inside of the first tube and extending above the first outer tube. The lower ends of the tubes are adaptable for fastening means and the inside tube extends below the end of the first outer tube. Delivery and placement of a bifurcated graft is illustrated. U.S. Pat. No. 5,522,883 issued to Slater et al. describes an endoprosthesis stent/graft deployment system which includes a tubular delivery catheter, a radially expandable prosthesis positioned over the catheter, a removable endoprosthesis support assembly located adjacent the catheter opening and having an arm extending through the catheter which keeps the endoprosthesis in a compressed state, and a release mechanism insertable through the catheter for removing the support assembly.

U.S. Pat. No. 5,104,399 issued to Lazarus also describes an artificial graft and delivery method. The delivery system includes a capsule for transporting the graft through the blood vessel, a tube connected to the vessel which extends exterior to the vessel for manipulation by a user, and a balloon catheter positioned within the tube. Finally, U.S. Pat. No. 5,489,295 issued to Piplani et al. discloses a bifurcated graft and a method and apparatus for deploying the bifurcated graft. The Piplani et al. graft includes a main tubular body, first and second tubular legs joined to the main tubular body in a bifurcation, a first expandable attachment means for anchoring the main body located adjacent the opening for the first body, and a second expandable attachment means located adjacent the opening of the first tubular leg for anchoring the first tubular leg. The graft is intraluminally implanted using a catheter that is inserted into the aortic bifurcation through a first iliac artery so that the first attachment means adjacent the opening of the main body can be anchored in the aorta and the second attachment means adjacent the opening of the first tubular leg can be anchored in the first iliac artery. The second tubular leg is deployed into the second iliac artery by using a pull line attached to the second tubular leg. The Piplani et al. patent also discloses a deployment device consisting of a capsule catheter, a balloon catheter, and a separate expandable spring attachment means.

The previously described deployment methods, systems and devices do not allow for a bifurcated graft which is fully supported with self expandable stents to be delivered and implanted within an arterial bifurcation. A use of any of the previously described deployment devices or systems to implant the structural supported bifurcated graft of the present invention would result in failure due to the inability of those devices and systems to deliver and anchor the second supported limb within the second iliac artery. The previously described methods and systems simply do not allow for the delivery and implantation of a bifurcated vascular graft whose three open ends are supported by stents. Accordingly, not only is there a need for a structurally supported stable and durable bifurcated graft which is not susceptible to migration and leaking, but there is also a need for a delivery apparatus and method for deploying and implanting such a bifurcated graft.

SUMMARY OF THE INVENTION

It is a principal object of the present invention to provide a bifurcated vascular graft and a method and apparatus for deploying the bifurcated vascular graft.

It is another object of the present invention to provide a bifurcated vascular graft having partial structurally supported limbs which will not deform, twist, or collapse thereby preventing the obstruction of blood flow through the limbs of the bifurcated vascular graft.

It is yet another object of the present invention to provide a bifurcated vascular graft having a structurally supported main graft body which lends support to an unsupported portion of the limbs of the bifurcated vascular graft in order to prevent migration of the bifurcated vascular graft.

It is still another object of the present invention to provide a structurally supported, physically stable bifurcated vascular graft which will occlude small blood vessels from bleeding into the bifurcated vascular graft area.

It is still another object of the present invention to provide a bifurcated vascular graft having separate limb channels thereby allowing for partial deployment of the bifurcated graft. The advantage of this design can be seen when one limb of the graft fails to deploy due to anatomic or structural problems. In that event, the successfully deployed graft limb will be capable of routing blood to the occluded limb by way of a femoral-femoral bypass. Most of the present bifurcated graft designs are not recoverable in this way and their failure to deploy usually forces a conversion to classic surgery.

It is yet another object of the present invention to provide a method and apparatus for deploying any one-piece bifurcated graft, including the bifurcated vascular graft of the present invention, within the body of a patient.

Still another object of the present invention is to provide a method and apparatus for intraluminally deploying a one-piece bifurcated graft, including the bifurcated vascular graft of the present invention, within a patient's body which is simple and efficient.

Yet another object of the present invention is to provide a method and apparatus for repairing an abdominal aortic aneurysm which is noninvasive and which does not require suturing of the graft to the aortic wall or iliac arteries.

In brief, the bifurcated vascular graft of the present invention includes:

a hollow tubular body member having first and second open ends;

a first hollow tubular limb member having first and second open ends; and a second hollow tubular limb member having first and second open ends wherein the first open end of each of the first and second hollow tubular limb members is connected to the hollow tubular body member near the first open end of the hollow tubular body member such that a length of the limb members are circumferentially contained within the hollow tubular body member.

The bifurcated vascular graft may include stents or similar support structures that are placed adjacent to the three openings contained in the bifurcated vascular graft. One stent may be positioned such that it encompasses the entire interior surface of the hollow tubular body member while two additional stents may be positioned about the exterior surface near the second ends of the first and second hollow tubular limb members, respectively. Cuffs may also be formed at the ends of these limb members by folding the second ends of the grafts back over the stents.

A method for making the bifurcated vascular graft of the present invention includes the steps of:

a) cutting about a middle circumference of a thin hollow tube until approximately ¾ of the circumference is cut;

b) folding the thin hollow tube at the cut away from the uncut portion to form two hollow tubular limb members having equal diameters which are attached to one another along the fold;

c) positioning the hollow tubular limb members within a hollow tubular body member having a diameter at least twice the diameter of the hollow tubular limb members; and d) attaching the cut ends of the hollow tubular limb members to an end of the hollow tubular body member such that a length of the limb members are circumferentially contained within the hollow tubular body member.

The method may also include the steps of positioning a first structural support adjacent the end of the hollow tubular member containing the attachment of the cut ends of the two hollow tubular members wherein the first structural support is located about an interior of the hollow tubular member, and positioning second and third structural supports about an exterior of the two hollow tubular limb members, respectively, at ends of the two hollow tubular limb members that are opposite the fold.

In another aspect of the present invention, the preferred apparatus for deploying a bifurcated vascular graft within the body of a patient includes:

a first limb tube for loading the first limb;

a second limb tube for loading the second limb wherein the first and second loaded limb tubes are positioned parallel to one another;

a graft body tube for loading the main graft body wherein the graft body tube is positioned adjacent to parallel ends of the first and second limb tubes; and an outermost tube for loading the first and second limb tubes and the graft body tube such that all of said tubes are contained within the outermost tube.

Another embodiment of the deployment apparatus includes first and second limb tube members which can both be inserted into the graft body tube at the same time. The deployment apparatus may also include a metal tube and guide wire which are insertable throughout an entire length of the apparatus. The first and second limb tubes have approximately equal diameters and the second limb tube is preferably shorter than the first limb tube.

Finally, the method of the present invention for intraluminally delivering a bifurcated vascular graft having a main graft body which bifurcates into first and second limbs within a patient's body includes the steps of a) loading the first and second limbs and the main graft body into separate tubes, b) inserting the tubes endoluminally within the patient, c) positioning the tubes within the patient, and d) deploying the limbs and the main body graft one at a time by removing their respective tubes. One example in which this simple and noninvasive method may be used is in the repair of an abdominal aortic aneurysm.

Additional objects, features and advantages of the varying aspects of the present invention will become more apparent from the following description in which the preferred embodiments of the present invention are set out in detail in conjunction with the accompanying drawings.

BRIEF DESCRIPTION OF THE DRAWINGS

In the drawings, which illustrate the best mode presently contemplated for carrying out the invention.

FIG. 2 is a perspective view of the structurally supported bifurcated vascular graft of the present invention with structural stent supports located on the interior of the graft shown in phantom. Portions of the hollow tubular limb members of the bifurcated vascular graft are also shown in phantom.

FIG. 3 is a right end view of the structurally supported bifurcated vascular graft of the present invention which is taken from the proximal end of the bifurcated vascular graft which includes the main tubular body of the graft.

FIG. 4 is a cross-sectional view taken along line 4—4 of FIG. 3.

FIG. 5 is a partial cross-sectional view of the deployment apparatus of the present invention with the structurally supported bifurcated vascular graft of the present invention shown loaded within the deployment apparatus of the present invention prior to deployment of the structurally supported bifurcated vascular graft.

FIG. 6A is a perspective view of a second hollow limb tube of the deployment apparatus of the present invention which holds the second hollow tubular limb member of the bifurcated vascular graft of the present invention during positioning, and prior to deployment, of the bifurcated vascular graft of the present invention.

FIG. 6B is a partial perspective view of a bifurcated blood vessel with the blood vessel shown cut away to illustrate the placement and positioning of the deployment apparatus of the present invention which contains the structurally supported bifurcated vascular graft of the present invention. Portions of the outermost tube of the deployment apparatus are also shown cut away to illustrate the position of the first and second limb tubes and graft body tube which comprise the deployment apparatus. A portion of the second limb tube is shown in phantom.

FIGS. 7A–7F are diagrams showing the method and apparatus of the present invention used for deploying the structurally supported bifurcated vascular graft of the present invention.

FIG. 7G is a partial perspective view of a bifurcated blood vessel shown cut away to illustrate the structurally supported bifurcated vascular graft of the present invention deployed and anchored in place within the bifurcated blood vessel.

DESCRIPTION OF THE PREFERRED EMBODIMENTS

Figure 1:
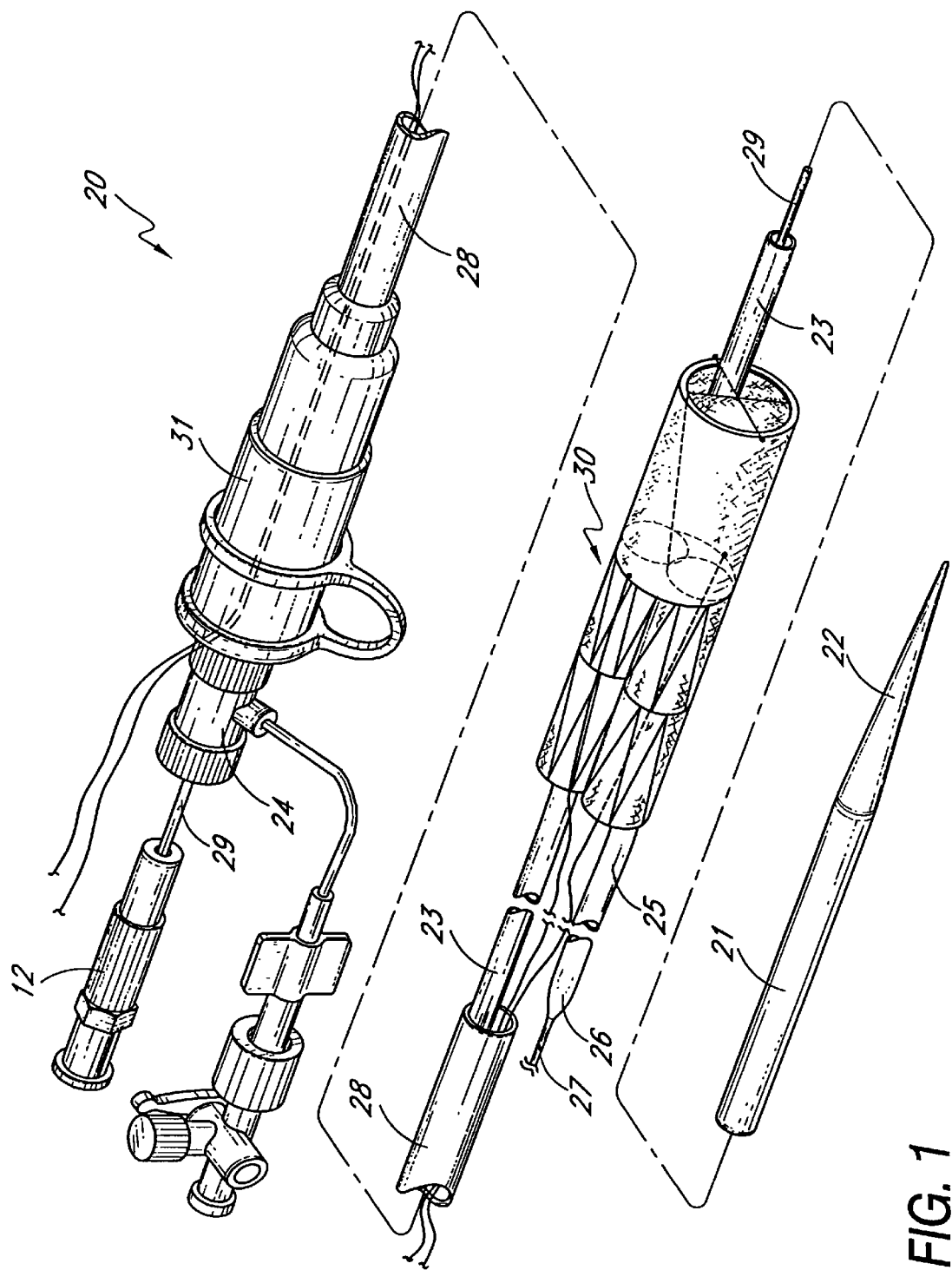
FIG. 1 is an exploded perspective view of the deployment apparatus of the present invention.

An exploded perspective view of the deployment apparatus 20 of the present invention is shown in FIG. 1. The deployment apparatus 20 includes a graft body tube 21 of variable length and diameter having a tapered tip 22, a first limb tube 23 of variable length and diameter which connects to a hemostatic valve 24, a second limb tube 25 of variable length and diameter having a tapered tip 26 and a guide wire 27 coming from the tapered tip, an outermost tube 28 of variable length and diameter which is large enough to contain the graft body tube 21 and the first and second limb tubes 23 and 25 at the same time and a homeostatic valve 31 connected to the outermost tube 28, and a small metal guide tube 29 of variable length and diameter which is large enough to allow a guide wire to pass therethrough. The metal guide tube 29 is attached to the graft body tube 21 within the graft body tube 21 near its tapered end 22 when the device is fully loaded and ready to deploy. A luer lock 12 is shown connected to the metal guide wire 29 and a three-way stopcock for adding and removing fluid is shown connected to the hemostatic valve 24 for the first limb tube 23. It should be noted that the deployment apparatus 20 of the present invention may be used to deploy any one-piece bifurcated graft, not just the bifurcated vascular graft 30 of the present invention.

FIG. 2 shows a perspective view of the bifurcated vascular graft 30 of the present invention. The bifurcated vascular graft 30 comprises a hollow tubular body member 32, a first hollow tubular limb member 34, and a second hollow tubular limb member 36. The hollow tubular body member 32 has a first open end 38 and a second open end 40. A first stent 42 is positioned about the interior of the hollow tubular body member 32 to support the hollow tubular graft body member 32. The first stent 42, or any other suitable biocompatible structural support, preferably encompasses the entire interior surface area of the hollow tubular body member 32 in order to provide the necessary structural support. Further, the hollow tubular body member 32 may be completely supported by attaching several stents along the entire length of the hollow tubular body member 32.

The first and second hollow tubular limb members 34 and 36 have approximately equal diameters, each of which is less than the diameter of the hollow tubular body member 32. The first hollow tubular limb member 34 comprises a first open end (not shown) and a second open end 44. Similarly, the second hollow tubular limb member 36 comprises a first open end (not shown) and a second open end 46. Second and third stents 48 and 50, respectively, are positioned adjacent the second ends 44 and 46 of the first and second hollow limb members 34 and 36 such that they each cover an exterior portion of their respective limb members 34 and 36. The second and third stents 48 and 50 only encompass that portion of their respective limb members 34 and 36 which extend from the second end 40 of the hollow tubular body member 32. Alternatively, the second and third stents 48 and 50 may encompass the entire first and second hollow tubular limb members 34 and 36 by extending along their entire lengths. Further, as previously explained with reference to the first stent 42, the second and third stents 48 and 50 may each comprise a plurality of stents or structural supports. Also, these stents may support the first and second hollow tubular limb members 34 and 36 either externally or internally.

The first and second hollow tubular limb members 34 and 36 are circumferentially contained within the hollow tubular body member 32 such that a portion of the hollow tubular limb members 34 and 36 transverse the length of the hollow tubular body member 32. As, previously explained, the support structures used to provide external structural support to those portions of the hollow tubular limbs 34 and 36 which extend beyond the second end 40 of the hollow tubular body member 32 may comprise one or more self expanding stents of varying lengths or any other suitable biocompatible structural support that will self expand to a surrounding vessel diameter. The second and third stents 48 and 50 are joined and anchored to the first stent 42 to form joints 49 and 51. This configuration prevents twisting and/or misalignment of the limbs 34 and 36 of the graft 30.

When loading the bifurcated vascular graft 30 onto the deployment apparatus 20 of the present invention, the first hollow tubular limb member 34 is loaded into the first limb tube 23, the second hollow tubular limb member 36 is loaded into the second limb tube 25, and the hollow tubular body member 32 is loaded into the graft body tube 21. In a preferred embodiment, the loaded first and second limb tubes 23 and 25 may be dimensioned such that they will lie end to end with the loaded graft body tube 21. Alternatively, the loaded first and second limb tubes 23 and 25 may be of a small enough diameter such that they can be inserted into the interior of the graft body tube 21 so that they can contain the entire length of the respective first and second hollow tubular limb members 34 and 36 within the graft body tube 21. The loaded graft body tube 21 and the loaded first and second limb tubes 23 and 25 are then all loaded into the outermost tube 28 which is connected to a homeostatic valve 31. The metal tube 29 containing a guide wire (not shown), separate and distinct from the guide wire 26 connected to the second limb tube 25, can be inserted through the entire loaded apparatus.

Turning now to FIG. 3., a right end view of the structurally supported bifurcated vascular graft 30 of the present invention is shown with the right end view taken from the proximal end of the bifurcated vascular graft. As can be seen from FIG. 3, the first and second hollow tubular limb members 34 and 36 are connected to one another along a diameter of the hollow tubular body member 32 which divides the lumen of the hollow tubular body member 32 in half. The first and second hollow tubular limb members 34 and 36 include first and second lumens 52 and 54, respectively, which are approximately equal to one another area and which fit inside of the lumen of the hollow tubular body member 32. The first open ends 56 and 58 of the hollow tubular limb members 34 and 36, respectively, can be seen from this right end view of the bifurcated vascular graft 30. Those portions of the circumference of the first open ends 56 and 58 of the first and second hollow tubular limbs 34 and 36 which are not attached to one another are connected to the circumference of the first open end 38 of the of the hollow tubular body member 32. The first stent 42 is located about the interior surface area of the hollow tubular body member 32 and is thereby contained between the interior of the hollow tubular body member 32 and the exteriors of the first and second hollow tubular limbs 34 and 36.

That portion of the circumference of the first ends 56 and 58 of the first and second hollow tubular limbs 34 and 36 which are attached to one another may be supported by a cross support stitch or support suture 60 which is positioned underneath the attached area and within the interior of the hollow tubular body member 32. Another stitch or suture 57 is placed across the diameter of the second end 40 of the hollow tubular body member 32 such that the ends 59 and 61 of the suture are left to trail from the second end 40 of the body member 32 in order to aid in the deployment of the bifurcated vascular graft 30.

A cross-sectional view of the bifurcated vascular graft 30 of the present invention taken along line 4—4 of FIG. 2 is shown in FIG. 3. The first ends 56 and 58 of the first and second hollow tubular limbs 34 and 36 are attached to the first end 38 of the hollow tubular body member 32 such that the first and second hollow tubular limbs 34 and 36 are partially contained within the lumen of the hollow tubular body member 32. The first stent 42 (or structural support) is positioned about the interior surface of the lumen of the hollow tubular body member 32 and is thereby contained between the interior surface of the hollow tubular body member 32 and the exterior surfaces 62 and 64 of the first and second hollow tubular limb members 34 and 36, respectively. The second and third stents 48 and 50 (or structural supports) are positioned adjacent the second ends 44 and 46 of the first and second hollow tubular limb members 34 and 36, respectively, such that they encompass a portion of the exterior surfaces 62 and 64 of the first and second hollow tubular limb members 34 and 36, respectively. Also, as previously described, the first and second hollow tubular limb members 34 and 36 may be structurally supported with stents along their entire length.

FIG. 5 shows a partial cross-section of the deployment apparatus 20 of the present invention with the bifurcated vascular graft 30 of the present invention loaded within the deployment apparatus 20 prior to deployment of the graft 30. The first hollow tubular limb member 34 of the bifurcated vascular graft 30 is shown loaded into the first limb tube 23 and the second hollow tubular limb member 36 of the bifurcated vascular graft 30 is shown loaded into the second limb tube 25. The hollow tubular body member 32 of the bifurcated vascular graft 30 is shown loaded into the graft body tube 21 which is tapered at its second end 70 in order to allow for easier movement through the blood vessels and easier re-entry of the graft body tube 21 into the outermost tube 28.

The loaded first and second limb tubes 23 and 25 and the loaded graft body tube 21 are all loaded within the outermost tube 28. The first ends 72 and 74 of the loaded first and second limb tubes 23 and 25 may lie adjacent the second end 70 of the loaded graft body tube 21 if the second end 70 of the graft body tube 21 is not tapered. However, if the second end 70 of the graft body tube 21 is tapered as shown in FIG. 5, the first ends 72 and 74 of the loaded first and second limb tubes 23 and 25 will not lie in adjacent vertical alignment with the second end 70 of the graft body tube 21. Nevertheless, this configuration of the tubes contained in the deployment apparatus 20 will not affect the successful deployment of a one-piece bifurcated graft from the deployment apparatus 20. The first and second limb tubes 23 and 25 may also be dimensioned such that they can both be inserted within the interior of the graft body tube 21 at the same time.

A perspective view of the second hollow limb tube 25 of the deployment apparatus 20 of the present invention is shown in FIG. 6A. The second hollow tube 25 includes a tapered tip 26, which may be removable, and a guide wire 27 that is attached to the tapered tip 26. The second hollow tubular limb member 34 of the bifurcated vascular graft 30 is loaded into the first end 74 of the second hollow limb tube 25 prior to inserting the deployment apparatus into a patient's body and implanting the graft 30.

FIG. 6B shows a partial view of a bifurcated blood vessel 80 shown cut away to illustrate the placement and positioning of the deployment apparatus 20 of the present invention. Portions of the outermost tube 28 of the deployment apparatus 20 are also shown cut away to illustrate the positions of the various other tubes which comprise the deployment apparatus 20. The first limb tube 23 contains the first hollow tubular limb member 34 of the bifurcated vascular graft 30, or any other one-piece bifurcated graft, and the second limb tube 25 contains the second hollow tubular limb member 36 of the bifurcated vascular graft 30, or any other one-piece bifurcated graft. The first and second limb tubes 23 and 25 lie parallel to one another and adjacent to the graft body tube 21 which contains the graft body member 32 of the bifurcated vascular graft 30, or any other one-piece bifurcated graft. The first and second limb tubes 23 and 25 and the graft body tube 21 are all contained within the outermost tube 28 of the deployment apparatus 20. In FIG. 6B, the outermost tube 28 has been pulled away from the bifurcation of the blood vessel thereby exposing almost the entire graft body tube 21. The guide wire 27 which is attached to the second limb tube 25 is passed to the left side 82 of the bifurcated blood vessel 80.

FIG. 7A shows the deployment apparatus 20 of the present invention in the same position within the blood vessel 80 as that shown in FIG. 6B with the exception that a longer portion of the blood vessel 80 is shown to illustrate the position of the entire graft body tube 21 within the non-bifurcated portion of a bifurcated blood vessel such as the aorta. Techniques commonly known in the prior art are used to place the deployment apparatus 20 and the guide wire 27 at the position shown in FIG. 7A. First, access of both iliac (or femoral) arteries is obtained and sheaths with homeostatic valves are inserted into the left and right common femoral (or left and right common iliac) arteries. A separate guide wire is then passed proximally into the aorta from the right sheath. Using a "cross-over" technique, an additional guide wire is brought from the left iliac (or femoral) sheath to the right iliac (or femoral) sheath. Following this, an angiographic catheter is passed from left to right over the guide wire. The wire is then removed, leaving the angiographic sheath protruding from the right sheath. The right sheath is then removed leaving the angiographic catheter and the aortic guide wire protruding from the artery through the patient's skin. Digital pressure is applied for homeostasis.

The guide wire 27 contained in the delivery apparatus 20 is inserted into the angiographic catheter and passed to the sheath in the left side and withdrawn until at least ⅔ to ¾ of the wire 27 is on the left side. The deployment apparatus 20 is then loaded onto the second aortic guide wire on the right side. In a simultaneous fashion, the deployment apparatus 20 is passed cephalad on the aortic wire (not shown) within the aorta while the second wire 27 on the left is withdrawn further to remove the slack which will occur as the deployment apparatus 20 moves in a cephalad or proximal manner as shown. Reverse positioning of the guide wires, catheters and sheaths are carried out when opposite side deployment is carried out, i.e. when the deployment apparatus 30 is inserted into the opposite bifurcated blood vessel.

Under fluoroscopic visualization, when the second limb tube 25 of the deployment apparatus 20 containing the guide wire 27 reaches the aortic bifurcation, all of the slack in the guide wire 27 will be gone and the guide wire 27 will appear as if it is coming almost straight from the side of the deployment apparatus 20. At that time, the outermost tube 28 is retracted thereby exposing the first and second limb tubes 23 and 25, which contain the first and second hollow tubular limb members 34 and 36, as shown in FIG. 7B. Further traction of the guide wire 27 will then remove more of the guide wire 27 which is folded upon itself within the graft body tube 21 as shown in FIG. 6B. Positioning of the deployment apparatus 20 by further movement of the apparatus 20 in a proximal and distal fashion with further gentle traction of the guide wire 27 will move the second limb tube 25 through the bifurcation and into the left iliac artery 82 as shown in FIGS. 7B through 7C.

Satisfactory positioning of the deployment apparatus 20 is obtained using fluoroscopic visualization such that the graft body tube 21 is located near the bifurcation and below the renal arteries with the first and second limb tubes 23 and 25 extending into the right and left iliac arteries 84 and 82. The first and second hollow tubular limb members 34 and 36 of the bifurcated vascular graft 30 are deployed by pulling the first and second limb tubes 23 and 25 distally (or caudad) as shown in FIGS. 7D and 7C. This process will uncover the first and second hollow tubular limb members 34 and 36 which have been loaded into the first and second limb tubes 23 and 25 by compressing the second and third stents 48 and 50 which surround the first and second hollow tubular limb members 34 and 36, respectively. The self expanding second and third stents 48 and 50 will then expand to the surrounding vessel diameter of the right and left iliac arteries 84 and 82. Next, the first limb tube 23, which is longer than the second limb tube 25, is retracted back over the metal tube 29 while the second limb tube 25 is pulled through the sheath which still remains on the left side as previously described above with reference to the "cross over" technique.

Next, the ends 59 and 61 of the suture 57 which is sewn to the second end 40 of the hollow tubular body member 32 of the bifurcated vascular graft 30 are held firmly for counter traction while the metal tube 29 attached to the tapered tip 21 of the graft body tube 21 is pushed in a cephalad direction to expose and deploy the hollow tubular body member 32 of the bifurcated vascular graft 30. The compressed first stent 42 is thereby released and self expands to the diameter of the aorta.

The bifurcated vascular graft 30 of the present invention is now fully deployed. The first limb tube 23 is then pushed cephalad into the graft body tube 21 for a variable distance until a tapered bulb having the same diameter of the graft body tube 21 enters the caudad end of the graft body tube 21 to form a smooth tapered end to the graft body tube 21 so that it will retract easily through the limb members 34 and 36 of the bifurcated vascular graft 30.

The bifurcated vascular graft of the present invention may be comprised of any fabric or plastic materials while the stents or support structures contained in the graft may be comprised of any suitable biocompatible material capable of strengthening the graft. The deployment apparatus may be comprised of any suitable biocompatible material including plastics.

While the foregoing embodiments of the present invention have been set forth in detail for the purposes of making a complete disclosure of the invention, the above-described embodiments of the invention are intended to be illustrative only. Numerous alternative embodiments may be devised by those skilled in the art without departing from the spirit and scope of the following claims.

I claim:

1. A deployment apparatus for deploying a bifurcated graft having a main graft body which bifurcates at a junction into first and second limbs, the deployment apparatus comprising:
    a first tube for constraining and surrounding the first limb;
    a second tube for constraining and surrounding the second limb;
    a third tube for constraining and surrounding the main graft body, wherein at least one of said first, second and third tubes is adapted to constrain and surround the bifurcated graft in the area of the junction of the main graft body and the first and second limbs; and
    an outermost tube for surrounding the first, second and third tubes.

2. The deployment apparatus of claim 1 further comprising a metal tube for containing a guide wire wherein the metal tube is insertable throughout an entire length of the apparatus.

3. The deployment apparatus of claim 1 further comprising a first homeostatic valve connected to said first tube.

4. The apparatus of claim 3 further comprising a second homeostatic valve connected to said outermost tube.

5. The apparatus of claim 1 further comprising a tapered tip capable of fitting onto an open end of said third tube.

6. The apparatus of claim 1 wherein said second tube comprises a first open end, a second closed tapered end and a guide wire attached to said tapered end.

7. The apparatus of claim 6 wherein said second tube is shorter in length than said first tube.

8. The apparatus of claim 1 wherein said first tube has a first diameter and said second tube has a second diameter and the first and second diameters are approximately equal.

9. A deployment apparatus for deploying a bifurcated graft having a main graft body which bifurcates at a junction into first and second limbs, the deployment apparatus comprising:
    a first tube for constraining and surrounding the first limb;
    a second tube for constraining and surrounding the second limb; and
    an outermost tube for surrounding the first and second tubes and the main graft body wherein at least one of said first, second and outermost tubes is adapted to constrain and surround the bifurcated graft in the area of the junction of the main graft body and the first and second limbs.

10. The deployment apparatus of claim 9 further comprising a metal tube for containing a guide wire wherein the metal tube is insertable throughout an entire length of the apparatus.

11. The deployment apparatus of claim 9 further comprising a first homeostatic valve connected to said first tube.

12. The apparatus of claim 11 further comprising a second homeostatic valve connected to said outermost tube.

13. The apparatus of claim 9 further comprising a tapered tip capable of fitting onto an open end of said outermost tube.

14. The apparatus of claim 9 wherein said second tube comprises a first open end, a second closed tapered end and a guide wire attached to said tapered end.

15. The apparatus of claim 14 wherein said second tube is shorter in length than said first tube.

16. The apparatus of claim 9 wherein said first tube has a first diameter and said second tube has a second diameter and the first and second diameters are approximately equal.

17. A deployment apparatus as in claim 1, wherein the third tube is positioned distally of the first and second tubes.

18. A deployment apparatus as in claim 17, wherein the second tube has an open distal end for receiving the second limb of the graft and a closed proximal end.

19. A deployment apparatus as in claim 18, further comprising a wire attached to the closed proximal end so that proximal retraction of the wire will retract the second tube proximally with respect to the third tube to release the second limb.

20. A deployment apparatus as in claim 1, wherein the third tube has an open proximal end so that distal advancement of the third tube releases the main graft body.

21. A deployment apparatus as in claim 20, further comprising a tapered tip on the distal end of the third tube.

22. A deployment apparatus as in claim 9, wherein the outermost tube is positioned distally of the first and second tubes.

23. A deployment apparatus as in claim 22, wherein the second tube has an open distal end for receiving the second limb of the graft and a closed proximal end.

24. A deployment apparatus as in claim 23, further comprising a wire attached to the closed proximal end so that proximal retraction of the wire will retract the second tube proximally with respect to the outermost tube to release the second limb.

25. A deployment apparatus as in claim 9, wherein the outermost tube has an open proximal end so that distal advancement of the outermost tube releases the main graft body.

26. A deployment apparatus as in claim 25, further comprising a tapered tip on the distal end of the outermost tube.

* * * * *